United States Patent [19]

Reichmann et al.

[11] Patent Number: 4,652,493

[45] Date of Patent: Mar. 24, 1987

[54] SELF-CURING MATERIAL FOR THE PRODUCTION OF A WEATHER-RESISTANT, NON-YELLOWING SUPPORT BANDAGE

[75] Inventors: Wolfgang Reichmann, Duesseldorf, Fed. Rep. of Germany; Günther Lehnert, Berkeley, Calif.

[73] Assignee: Bayer Aktiengesellschaft, Leverkusen, Fed. Rep. of Germany

[21] Appl. No.: 371,149

[22] Filed: Apr. 23, 1982

Related U.S. Application Data

[63] Continuation of Ser. No. 151,059, May 19, 1980, abandoned.

[30] Foreign Application Priority Data

May 25, 1979 [DE] Fed. Rep. of Germany ....... 2921163

[51] Int. Cl.$^4$ .................. B32B 27/40; B32B 17/00; A61F 5/04
[52] U.S. Cl. ................... 428/423.1; 128/90; 428/262; 428/264; 428/286; 428/411.1; 428/425.1; 428/425.6; 427/2
[58] Field of Search ............... 428/425.6, 423.1, 320, 428/262, 264, 286, 411, 425.1; 260/45.9 NC, 45.8 N; 128/90, 91 A

[56] References Cited

U.S. PATENT DOCUMENTS

| | | | |
|---|---|---|---|
| 3,637,745 | 1/1972 | Heller | 260/45.8 N |
| 3,808,273 | 4/1974 | Burdet | 260/45.9 NC |
| 3,906,033 | 9/1975 | Biland | 260/45.9 NC |
| 4,003,875 | 1/1977 | Luthi | 260/45.9 NC |
| 4,020,832 | 5/1977 | Kirkpatrick | 128/90 |
| 4,160,686 | 7/1979 | Niederdellmann | 428/423.1 |
| 4,189,542 | 2/1980 | Kleiman | 524/124 |

FOREIGN PATENT DOCUMENTS

| | | |
|---|---|---|
| 2651089 | 11/1976 | Fed. Rep. of Germany . |
| 2737671 | 8/1977 | Fed. Rep. of Germany . |
| 1578895 | 11/1980 | United Kingdom . |

OTHER PUBLICATIONS

"New Fiber Glass Casting Systems", *Clinical Orthopaedics and Related Research*, 103, 109–117 (1974).

*Primary Examiner*—Ellis P. Robinson
*Attorney, Agent, or Firm*—Gene Harsh

[57] ABSTRACT

The disclosed invention is concerned with porous substrates impregnated with moisture curing polyurethane oligomers incorporating tertiary nitrogen atoms and free aromatic isocyanate groups in which the yellowing tendency of these isocyanates is diminished or supressed by the inclusion of specific light protection agents. These agents are either substituted oxalanilides or indole or indoline derivatives. The impregnated substrates cure rapidly when exposed to moisture to yield rigid structures suitable as a replacement for Plaster of Pairs in medicinal and veterinary bandaging applications.

6 Claims, No Drawings

SELF-CURING MATERIAL FOR THE PRODUCTION OF A WEATHER-RESISTANT, NON-YELLOWING SUPPORT BANDAGE

This application is a continuation of application Ser. No. 151,059, filed May 19, 1980, now abandoned.

BACKGROUND OF THE INVENTION

The use of bindings which are impregnated with gypsum as reinforcing bandage material is known. These gypsum bandages do not turn yellow, but they are undesirably heavy, are not very permeable to air, lose strength quickly in moist conditions, for example, during the action of water on the cured bandage, prevent X-ray photographs from being diagnosed owing to the X-ray absorption and scattering thereof and often give rise to skin irritations which are brought about by the growth of bacteria or fungi in the bandage owing to the poor resistance to water thereof.

There have therefore been a large number of attempts to provide bandage materials which do not suffer from these disadvantages. Thus, for example, attempts have been made to impregnate bandage material with polymer solution which may be cured by ultra-violet light and to cure the bandage produced from them by irradiating them with an ultra-violet lamp (Clinical Orthopaedics and Related Research 103, 109–117 (1974)). The operation with ultra-violet sources is complicated. Moreover, the ultra-violet light only reaches the upper layers of the bandage so that curing does not take place or demands a longer time in the deeper layers. Another serious disadvantage of this process lies in the fact that it is not possible to observe the site of fracture by X-ray control during the operation of curing by ultra-violet irradiation. Fast curing bindings based on polyurethane reactive systems and the use thereof for medical support bandages are described in German Offenlegungsschrift No. 2,651,089.

The bandages mentioned therein are usually dyed either by the reactive binding coating itself or by pigments or dyes used in the coating material. Colorless bindings may also be obtained by suitable choice of the starting components (for example, according to Example 12 of German Offenlegungsschrift No. 2,651,089), but they tend to turn yellow owing to the aromatic groups contained in the impregnation. These bandages therefore become unsightly after a very short period. As shown in Example 16 of German Offenlegungsschrift No. 2,651,089, the use of non-yellowing coating material leads to curing times which are unsuitably long for the desired application.

The present invention accordingly provides weather-resistant, substantially non-yellowing support bandages for medical or veterinary use, which no longer exhibit the disadvantages of the above-mentioned prior art materials. The support bandages according to the present invention have, in addition to the advantages mentioned in German Offenlegungsschrift No. 2,651,089, the further advantage of adequate stability to weather and light.

SUMMARY OF THE INVENTION

The present invention accordingly relates to a self-curing material for the production of weather-resistant, substantially non-yellowing support bandages for medical or veterinary use, comprising an air-permeable, flexible sheet which is impregnated or coated with from 50 to 300%, by weight, based on untreated sheet, of a NCO-prepolymer based on aromatic polyisocyanates and polyols containing tertiary amine nitrogen, wherein the prepolymers have an NCO content of from 5 to 30%, by weight, and a content of tertiary amine nitrogen of from 0.01 to 2.5%, by weight, which is characterized in that the NCO-prepolymer contains from 0.05 to 3%, by weight, preferably from 0.2 to 2%, by weight, of one of the light protection agents listed below:

(a) Substituted indolines corresponding to the following general formula:

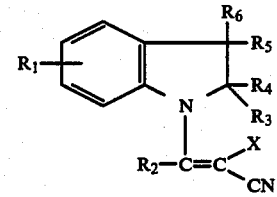

wherein $R_1$ represents a hydrogen atom or a methoxy group;

$R_2$ represents a hydrogen atom or a methyl group;

$R_3$ to $R_6$ each independently represents a hydrogen atom or a methyl group; or $R_4$ and $R_5$ may be conjoint giving a saturated 6 membered ring; and X represents a cyano group or a -COOR$_7$ group wherein $R_7$ represents an alkyl radical having from 1 to 8 carbon atoms; or a -CONR$_8$R$_9$ wherein $R_8$ and $R_9$ each independently represents a hydrogen atom or a methyl group;

and/or (b) Substituted oxalanilides corresponding to the following general formula:

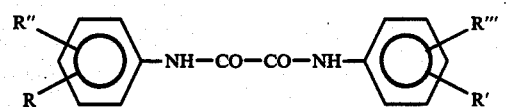

wherein

R and R' each independently represents an optionally branched alkyl or alkoxy radical having from 1 to 15, preferably from 1 to 8, carbon atoms; and R'' and R''' independently represents hydrogen or an optionally branched alkyl or alkoxy radical having from 1 to 15, preferably from 1 to 8, carbon atoms.

The stabilizers mentioned under (a) are preferred according to the present invention, in particular those wherein X represents an ester group. The production of these compounds is described in German Auslegeschrift No. 1,568,541 (U.S. Pat. No. 3,637,745).

DETAILED DESCRIPTION OF THE INVENTION

The bindings according to the present invention are air-permeable flexible sheets, preferably based on textiles, impregnated with specific isocyanate prepolymers containing light protection agents, and having a weight per unit area of from 20 to 1000, preferably from 30 to 500, gm/m$^2$. Suitable sheets of this type include for example (1). Woven knitted or hosiery textile fabrics having a weight per unit area of from 20 to 200 g/m$^2$, preferably from 40 to 100 g/m$^2$, having a preferred thread count of from 2 to 20 threads per linear centimeter in the longitudinal and transverse direction. The woven or knitted textile fabric may be produced from various natural or synthetic yarns. However, it is preferable to use knitted or woven fabrics which have been produced from mixed yarns which, in turn, have been obtained from hydrophobic threads and fibers having a high Emodulus (for example polyester), as well as hydrophilic natural or synthetic threads or fibers (for example cotton or polyamide).

(2). Woven, knitted or hosiery fabric made from glass fibers having a weight per unit area of from 60 to 500 g/m², preferably 100 to 400 g/m², and a preferred thread count of from 2 to 20 cm in the longitudinal and transverse direction. Woven glass fiber fabrics provided with a hydrophilic size are preferred.

(3). Unbonded or bonded or needle-felted non-woven fabrics based on inorganic and, preferably, organic fibers having a weight per unit area of from 30 to 400 g/m², preferably from 50 to 200 g/m².

Non-woven fabrics of the above-mentioned type having weights per unit area of up to 1000 g/m², are suitable for the production of reinforcing bandages according to the present invention in the form of shells or splints.

The woven, knitted or hosiery fabrics mentioned under (1). are particularly preferred.

Prepolymers which are suitable for impregnating the flexible sheets exemplified above include those which contain from 5 to 30%, by weight, preferably from 10 to 25%, by weight, of aromatically bound isocyanate groups, from 0.01 to 2.5%, by weight, preferably from 0.1 to 1.5%, by weight, of tertiary amine nitrogen and from 0.05 to 3%, by weight, preferably from 0.2 to 2% by weight, of light protection agents. Suitable selection of the viscosity of the starting materials for the production of the prepolymers also ensures that the prepolymers have a viscosity of from 3 to 50, preferably from 5 to 30, Pa.s/25° C.

The prepolymers containing light protection agents are produced in a known manner by the reaction of excess quantities of aromatic polyisocyanate with polyols containing tertiary amine nitrogen, the light protection agent being added as desired during production.

Suitable polyisocyanates include various colorless or slightly-colored aromatic polyisocyanates of the type described in "Polyurethanes: Chemistry and Technology," Part I, Interscience Publishers [1962) or in "Kunststoff Handbuch", Volume VII, Polyurethane, Carl-Hanser-Verlag, Munich (1966), for example 2,4-diisocyanato toluene or 2,6-diisocyanato toluene and mixtures thereof, 4,4'-diisocyanatodiphenyl methane or 2,4'-diisocyanatodiphenyl methane and mixtures thereof, optionally still containing small amounts of 2,2'-diisocyanatodiphenyl methane, diphenylmethane diisocyanates with one or more alkyl substituents at the aromatic nucleus or mixtures of the above-mentioned polyisocyanates.

Colorless or slightly-colored diisocyanatodiphenyl methane isomer mixtures are preferably used. Suitable polyols containing tertiary amine nitrogen include, for example, (1). Polyols which are free from ether groups and contain tertiary nitrogen having a molecular weight of from 105 to 300, such as N-methyl-diethanolamine, N-ethyl-diethanolamine, N-methyl-dipropanolamine, triethanolamine or tripropanolamine;

(2). Polyester polyols containing tertiary nitrogen having a molecular weight of from 300 to 4000, preferably from 800 to 2000, of the type which may be obtained by the reaction of polybasic acids with amino alcohols of the type exemplified above, optionally with simultaneous use of nitrogen-free polyhydric alcohols. Suitable polybasic acids include, for example, adipic acid, phthalic acid or hexahydrophthalic acid. Suitable nitrogen-free polybasic alcohols for the production of the polyesters include, for example, ethylene glycol, tetramethylene glycol, hexamethylene glycol, neopentyl glycol and trimethylol propane;

(3). Polyether polyols containing tertiary amine nitrogen and having molecular weights of from 300 to 4000, preferably from 800 to 2000, of the type which may be obtained in known manner by the alkoxylation of nitrogen-containing starter molecules. Suitable nitrogen-containing starter molecules include, for example, the aminoalcohols exemplified above, ammonia, or amines containing at least 2 N-H bonds, such as ethylene diamine, aniline, toluene diamine or hexamethylene diamine. Suitable alkylene oxides for the production of the polyethers include, for example, ethylene oxide or propylene oxide. It is particularly preferred to use the propoxylation products of the above-mentioned nitrogen-containing starter molecules.

It is known from German Offenlegungsschrift Nos. 2,737,670 and 2,737,671, to achieve the resistance of specific polyurethane foams to the influences of weather and light by using specific light protection agents (see also "Die Stabilisierung derKunststoffe gegen Licht und Wärme", J. Voigt, Springer Verlag (1966)). Light protection agents of this type which are known for use in polyurethane foams include, for example:

(I) Piperidine derivatives 4-benzoyloxy-, 4-salicycloyloxy-, 4-capryloxy-, 4-stearoyloxy-, 4-(β-3,5-di-t-butyl-4-hydroxy-phenyl-propionyloxy)-, 4-(3,5-di-t-butyl-4-hydroxybenzoxy)-2,2,6,6-tetramethylpiperidine; 4-benzoyloxy-, 4-salicyloyoxy-, 4-stearoyloxy and 4-t-butylbenzoyl-1,2,2,6,6-pentamethylpiperidine; bis-(2,2,6,6-tetramethyl-4-piperidyl)sebacate, bis-(2,2,6,6-tetramethyl-4-piperidyl)suberate, bis-(2,2,6,6-tetramethyl-4-piperidyl)dodecandioate, bis-(1,2,2,6,6-pentamethyl-4-piperidyl)-sebacate; 4-capryloyloxy-1-propyl-2,2,6,6-tetramethylpiperidine; 4-capryloyoxy-1-allyl-2,2,6,6-tetramethylpiperidine; 4-benzoylamido-, 4-acryloxyamido- and 4-stearoylamido-2,2,6,6-tetramethylpiperidine.

2,4,6-tris-(2,2,6,6-tetramethyl-4-piperidyloxy)-s-triazine, 2,4,6-tris-(1,2,2,6,6-pentamethyl-4-piperidyloxy)-s-triazine, 2,4,6-tris-(2,2,6,6-tetramethyl-4-piperidylamino)-s-triazine, 2,2,6,6-tetramethyl-4-β-cyanoethoxypiperidine, 1,2,2,6,6-pentamethyl-4-lauroyloxypiperidine and triacetone-aminoxime.

(II) Benzophenone derivatives 2,4-dihydroxy-, 2-hydroxy-4-methoxy-, 2-hydroxy-4-oxtoxy, 2-hydroxy-4-dodecyloxy-, 2-hydroxy-4-benzyloxy-, 2-hydroxy-4,4'-dimethoxy-, 2,4,4'-trihydroxy-, 2,2'-dihydroxy-4,4'-dimethoxy-, 2,2',4,4'-tetrahydroxy-, 2,2'-dihydroxy-4-methoxy-, 2-hydroxy-2'-carboxy-4-methoxy-, 2,2'-dihydroxy-4-oxtoxy- and 2,2'-dihydroxy-4-dodecyloxy-benzophenone.

(III) Benzotriazole derivatives 2-(2'-hydroxy-5'-methylphenyl)-, 2-(2'-hydroxy-5'-t-butylphenyl)-, 2-(2'-hydroxy-5'-t-octylphenyl)-, 2-(2'- hydroxy-3'-t-butyl-5'-methylphenyl)-, 2-(2'-hydroxy-3'-t-butyl-5'-methylphenyl)-5-chloro-, 2-(2'-hydroxy-3',5'-di-t-butylphenyl)-, 2-(2'-hydroxy-3',5'-di-t-butylphenyl)-5-chloro-, 2-(2'-hydroxy-3',5'-di-t-amylphenyl)-, 2-(2'-hydroxy-3',5'-di-t-amylphenyl)-5-chloro-, 2-(2'-hydroxy-3'-sec.-butyl-5'-t-butylphenyl)-, 2-(2'-hydroxy-3'-t-butyl-5'-sec.-butylphenyl)-, 2-(2',4'-dihydroxyphenyl)- 2-(2'-hydroxy-4'-methoxyphenyl)-, 2-(2'-hydroxy-4'-octoxyphenyl)-, 2-(2'-hydroxy-3'-α-phenylethyl-5'-methylphenyl)- and 2-(2'-hydroxy-3'-α-phenylethyl-5'-methylphenyl)-5-chloro-benztriazole.

(IV) Oxalanilides 2-ethyl-2'-ethoxy-, 2-ethoxy-2'-ethoxy-5'-t-butyl-, 2-ethyl-4-t-butyl-2'-ethoxy-5'-t-butyl-, 2,2'-dimethoxy-, 2,2'-diethoxy-, 2,2'-di-t-butyl-, 4,4'-dimethoxy-, 4,4'-diethoxy-, 2,4'-dimethoxy-, 2,4'-diethoxy-, 2-methoxy-2'-ethoxy-, 2-methoxy-4'-ethoxy-, 2-ethoxy-4'-methoxy-, 2,2'-dioctoxy-5,5'-di-t-butyl-, 2,2'-didodecyloxy-5,5'-di-t-butyl-, 2-ethyl-2'-octoxy-, 4,4'-di-octoxy-, 2-ethyl-2'-butoxy- and 4-methyl-4'-methoxy-oxalanilide.

(V) Salicylic acid phenyl ester and its derivatives salicylic acid phenyl ester, salicylic acid-4-t-butylphenyl ester and salicylic acid-4-t-octylphenyl ester.

(VI) Cinnamic acid ester derivatives

α-cyano-β-methyl-4-methoxycinnamic acid methyl ester, α-cyano-β-methyl-4-methoxycinnamic acid butyl ester, α-cyano-β-phenyl-cinnamic acid ethyl ester and α-cyano-β-phenylcinnamic acid isooctyl ester.

(VII) Malonic ester derivatives 4-methoxy-benzylidene-malonic acid dimethyl ester, 4-methoxy-benzylidene-malonic acid diethyl ester and 4-butoxy-benzylidenemalonic acid dimethyl ester.

(VIII) Indoline derivatives 2-methyl-1-[1-cyano-1-methoxy-carbonyl-ethene-(1)-yl-(2)]-indoline, 1-[1-cyano-1-ethoxy-carbonyl-ethene-(1)-yl-(2)]-indoline, 2,3-dimethyl-1-[1-cyano-1-methoxycarbonyl-ethene-(1)-yl-(2)]-indoline, 3-methyl-1-[1-cyano-1-carbonamido-ethene-(1)-yl-(2]-indoline, 2,2-dimethyl-1-[1-cyano-1-methoxy-carbonyl-2-methyl-ethene-(1)-yl-(2)]-indoline, 2,3-dimethyl-5-methoxy-1-[1,1-dicyano-2-methyl-ethene-(1)-yl-(2)]-indoline and 8-methoxy-1-[1-cyano-1-dimethylamido-carbonyl-ethene-(1)-yl-(2)]-indoline.

It has however surprisingly been found that the desired stabilizing effect in the support bandages according to the present invention may only be achieved satisfactorily when using light protection agents corresponding to the general formulae given above (corresponding to (IV) and (VIII))

The bindings according to the present invention may be impregnated with the prepolymers containing the exemplified light protection agents in various ways. The bindings are subjected, for example, to an impregnation or coating process using conventional apparatus, for example, by doctoring, impregnation and subsequent squeezing on rollers or centrifuging, by spraying or application by reversal methods. In this process, the prepolymer may either be used as a mass or as a solution. If it is used as a solution, readily volatile solvents, such as methylene chloride, are preferably used.

Suitable selection of the weight per unit area, the mesh width of the flexible substrate and the applied quantity of the prepolymer containing the light protection agent within the ranges given above ensures that the fiber materials are merely surrounded while maintaining pores in order to allow the desired breathing activity.

If auxiliary solvents are used, the impregnated substrate is freed from them, for example, by vacuum treatment. After impregnation, the bindings obtained according to the present invention may be stored in closed containers in the absence of moisture. The bindings according to the present invention are preferably stored in the form of wound bodies or are piled up in hermetically sealed containers made of metals, such as aluminum. Welded bags of polyethylene-coated aluminum foils or aluminum cans which are sealed tight to moisture, are particularly suitable for storing the bindings according to the present invention. The bindings may then be removed from the container at the desired moment.

During application of the bindings according to the present invention, the part of the body to be supported is initially covered with an air-permeable, unimpregnated lining. Suitable materials for this lining include, for example, open-pored paper, nonwoven fabrics or textile binding materials. Materials which exhibit only limited hydrophilic properties are preferably used as linings. A non-woven polyester or polypropylene fabric, for example, is therefore particularly suitable.

A binding according to the present invention which has previously been saturated with water is then wound onto the part of the body which has been covered with a lining in this way. The bindings to be used according to the present invention are saturated with water immediately before being used, for example, by immersing the bindings in water.

The thickness of the support bandage produced in this way is based on the respective medical requirements. It is generally from 3 to 10 mm. The bindings according to the present invention may be used for the production of support bandages by winding them round the parts of the body to be supported and may also be used, optionally in panel form, for the production of shells or splints.

The weather-resistant, non-yellowing support bandages according to the present invention are distinguished by the excellent mechanical properties thereof, in particular by a balanced relationship between rigidity and elasticity.

The following Examples illustrate the present invention. Quantities are to be interpreted as parts, by weight, and percentages, by weight, unless otherwise indicated.

EXAMPLES 1 to 5

Some 12 cm wide gauze bandages composed of a mixed yarn containing 40% cotton and 60% viscose and having a weight per unit area of 30 g/m$^2$ and a thread count of 12 threads per cm in the warp and 8 threads per cm in the weftwere each impregnated, in the absence of moisture, with 25 g of a prepolymer containing light protection agents (see Table below for type and quantity of light protection agent) composed of a diisocyanatodiphenylmethane isomer mixture (ratio, by weight, 4,4'-isomer: 2,4'-isomer=1:1.5) and propoxylated triethanolamine (OH number 148) in a ratio, by weight, of 1.25:1 (12% by weight, NCO groups, 0.5%, by weight, tertiary amine nitrogen), which was present as a solution in methylene chloride (ratio, by weight, of prepolymer: solvent=1:1). After impregnation, the solvent was removed in an oil pump vacuum and the impregnated bindings were wound on to a polyethylene reel or stacked up and sealed in a bag with a sealed edge composed of a three layer polyester/aluminum, polyethylene laminate.

After a storage time of one week at about 25° C., the impregnated bindings were taken from the packaging, immersed in water at about 25° C. for from three to five seconds and kneaded lightly. Tubular shaped articles of about 42 mm internal diameter and about 12 cm in length were then wound within 3 minutes.

With slight evolution of heat (surface temperature maximum 35° C.) the support bandages cured in a further 5 minutes to form stable shaped articles having a capacity for loads and excellent cohesion.

The cured support bandages were each irradiated with two analytical lamps of the TL20 W/08 type made by the Philips (wave length range from 300 to 400 mm, maximum intensity 350 mm) for 50 hours (using illuminost C) at a distance of 25 cm from the sample and with two of these analytical lamps arranged at a distance of 12 cm from the sample. The yellowing of the samples was measured using the Helmholtz indices of measurement in accordance with DIN 50 33.

The degree of yellowing is shown in the Table below.
The following light protection agents were examined:

EXAMPLE 1

2-methyl-1-[1-cyano-1-methoxycarbonyl-ethene-(1)-yl-(2)]-indoline.

EXAMPLE 2

2,2'-di-t-butyloxalanilide.

EXAMPLE 3

(comparison)

2(n-butyl)-2[3,5-di-t-butyl-benzyl-] malonic acid-di-(1,2,2,6,6-pentamethyl-4-piperidyl)-ester.

EXAMPLE 4

(comparison)

bis-(2,2,6,6-tetramethyl-4-piperidyl)-sebacate

EXAMPLE 5

(comparison)

2-(2'-hydroxy-5'-methylphenyl)-benztriazole

The numbers indicated under "optical impression" in the Table below represent:
1: no yellowing detected
2: very light yellowing
3: slight yellowing
4: noticeably yellowed
5: strongly yellowed.

Table

| Example | Concentration of the light protection agent (%) | Helmholtz-index of measurement Pc Irradiation Before | After | ΔPc | Optical impression |
|---|---|---|---|---|---|
| zero test | 0 | 0.073 | 0.46 | 0.39 | 5 |
| 1 a | 0.25 | 0.070 | 0.29 | 0.22 | 1 |
| b | 1 | 0.064 | 0.18 | 0.12 | |
| 2 a | 0.25 | 0.098 | 0.36 | 0.26 | 2 |
| b | 1 | 0.12 | 0.34 | 0.22 | |
| 3 a | 0.25 | 0.071 | 0.43 | 0.36 | 4 |
| b | 1 | 0.11 | 0.40 | 0.29 | |
| 4 | 1 | 0.085 | 0.45 | 0.37 | 5 |
| 5 | 1 | 0.085 | 0.52 | 0.44 | 5 |

Although the invention has been described in detail for the purpose of illustration, it is to be understood that such detail is solely for that purpose and that variations can be made therein by those skilled in the art without departing from the spirit and scope of the invention except as it may be limited by the claims.

What is claimed is:

1. A self-curing material for the production of weather-resistant, substantially non-yellowing support bandages for medical or veterinary use, comprising an air-permeable, flexible sheet which is impregnated or coated with from 50 to 300%, by weight, based on untreated sheet, of a NCO-prepolymer based on aromatic polyisocyanates and polyols containing tertiary amine nitrogen, wherein the prepolymers have a NCO content of from 5 to 30%, by weight, and a content of tertiary amine nitrogen of from 0.01 to 2.5%, by weight, characterized in that the NCO-prepolymer contains from 0.05 to 3%, by weight, (based on prepolymer) of:

(a) substituted indolines corresponding to the following general formula:

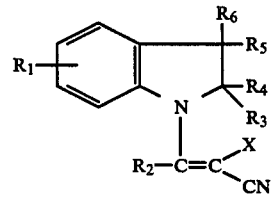

wherein
R$_1$ represents a hydrogen atom or methoxy group;
R$_2$ represents a hydrogen atom or a methyl group;
R$_3$ to R$_6$ each independently represents a hydrogen atom or a methyl group; or R$_4$ and R$_5$ may be conjoint giving a saturated 6 membered ring; and
X represents a cyano group or a —COOR$_7$ group wherein R$_7$ represents an alkyl radical having from 1 to 8 carbon atoms; or a —CONR$_8$R$_9$ group wherein R$_8$ and R$_9$ each independently represents a hydrogen atom or a methyl group; and/or (b) substituted oxalanilides corresponding to the following general formula:

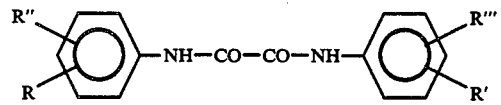

wherein
R and R' each independently represents an optionally branched alkyl or alkoxy radical having from 1 to 15 carbon atoms; and R" and R"' each independently represents hydrogen or an optionally branched alkyl or alkoxy radical having from 1 to 15 carbon atoms;
as light protection agent.

2. The material of claim 1, wherein the light protection agent corresponds to general formula (a) wherein X represents an ester group.

3. The material of claim 1, wherein the light protection agent is 2-methyl-1-[1-cyano-1-methoxycarbonylethene-(1)-yl-(2)]-indoline.

4. The material of claim 1, wherein the light protection agent is 2,2'-di-t-butyl oxalanilide.

5. The material of claim 1 wherein the light protection agent is selected from the group consisting of 2-ethyl-2'-ethoxy-, 2-ethoxy-2'-ethoxy-5'-t-butyl-, 2-ethyl-4-t-butyl-2'-ethoxy-5'-t-butyl-, 2,2'-dimethoxy, 2,2'-diethoxy-, 2,2'-di-t-butyl-, 4,4'-dimethoxy-, 4,4'-diethoxy-, 2,4'-dimethoxy-, 2,4' diethoxy-, 2-methoxy-2'-ethoxy-, 2-methoxy-4'-ethoxy-, 2-ethoxy-4'-methoxy-, 2,2'-dioctoxy-5,5'-di-t-butyl-, 2,2'-didodecyloxy-5,5'-di-t-butyl-, 2-ethyl-2'-oxtoxy-, 4,4'-di-octoxy-, 2-ethyl-2'-butoxy- and 4-methyl-4'-methoxy-oxalanilide and mixtures thereof.

6. The material of claim 1 wherein the light protection agent is 2-methyl-1-[1-cyano-1-methoxy carbonylethene-(1)-yl-(2)]-indoline.

* * * * *